United States Patent
Kawashima et al.

(10) Patent No.: US 8,088,817 B2
(45) Date of Patent: Jan. 3, 2012

(54) PYRROLE DERIVATIVE HAVING, AS SUBSTITUENTS, UREIDO GROUP, AMINOCARBONLY GROUP AND BICYCLIC GROUP WHICH MAY HAVE SUBSTITUENT

(75) Inventors: Kenji Kawashima, Ikoma (JP); Noriko Kawashima, Ikoma (JP); Hiroshi Enomoto, Ikoma (JP); Minoru Yamamoto, Ikoma (JP); Masaaki Murai, Ikoma (JP)

(73) Assignee: Santen Pharmaceutical Co., Ltd., Osaka-Shi, Osaka (JP)

( * ) Notice: Subject to any disclaimer, the term of this patent is extended or adjusted under 35 U.S.C. 154(b) by 0 days.

(21) Appl. No.: 12/737,807

(22) PCT Filed: Aug. 25, 2009

(86) PCT No.: PCT/JP2009/064744
§ 371 (c)(1),
(2), (4) Date: Feb. 17, 2011

(87) PCT Pub. No.: WO2010/024227
PCT Pub. Date: Mar. 4, 2010

(65) Prior Publication Data
US 2011/0136794 A1    Jun. 9, 2011

(30) Foreign Application Priority Data
Aug. 25, 2008    (JP) .................... 2008-214773

(51) Int. Cl.
*A61K 31/4025* (2006.01)
*A61K 31/401* (2006.01)
*C07D 207/34* (2006.01)
*C07D 405/04* (2006.01)
*C07D 409/04* (2006.01)

(52) U.S. Cl. ......... 514/422; 514/426; 548/522; 548/558

(58) Field of Classification Search .................... None
See application file for complete search history.

(56) References Cited

U.S. PATENT DOCUMENTS

| | | | |
|---|---|---|---|
| 7,098,240 | B2 | 8/2006 | Griffiths et al. |
| 7,358,376 | B2 | 4/2008 | Baxter et al. |
| 2004/0235821 | A1 | 11/2004 | Griffiths et al. |
| 2010/0099675 | A1 | 4/2010 | Kawashima et al. |

FOREIGN PATENT DOCUMENTS

| | | |
|---|---|---|
| JP | 2003-522766 A | 7/2003 |
| JP | 2004-536869 A | 12/2004 |
| WO | WO 03/086371 A2 | 10/2003 |
| WO | WO 2005/123671 A2 | 12/2005 |
| WO | WO 2008/087933 A1 | 7/2008 |
| WO | WO 2008/105408 A1 | 9/2008 |

OTHER PUBLICATIONS

Podolin, P.L. et al., "Attenuation of Murine Collagen-Induced Arthritis by a Novel, Potent, Selective Small Molecule Inhibitor of IκB Kinase 2, TPCA-1 (2-[Aminocarbonyl)amino]-5-(4-flurophenyl)-3-thiophenecarboxamide), Occurs via Reduction of Proinflammatory Cytokines and Antigen-Induced T Cell Proliferation," *Journal of Pharmacology and Experimental Therapeutics*, 2005, vol. 312, No. 1, pp. 373 to 381.
Bessatsu Igaku no Ayumi, *Journal of Clinical and Experimental Medicine, Supplement*, Cytokines, . . . (from Basic Clinical Research), 28-35 (1992).
K. Izumi et al., "Suppression of Choroidal Neovascularization by Blocking Interleukin-6 Receptor Signaling," *Invest. Ophthalmol. Vis. Sci.*, 47, E-Abstract 905 (2006).
Naoto Nakamura et al., "Increased concentration of pentosidine, an advanced glycation end product, and interleukin-6 in the vitreous of patients with proliferative diabetic retinopathy," *Diabetes. Res. Clin. Pract.* 61, 93-101 (2003).
Hideharu Funatsu et al., "Vitreous Levels of Interleukin-6 and Vascular Endothelial Growth Factor Are Related to Diabetic Macular Edema," *Ophthalmology*, 110, 1690 to 1696 (2003).
STN Registry files CAS No. 375823-41-9, (Apr. 8, 2007).
M. Teresa Garcia-Lopez et al., "New Routes for the Synthesis of Pyrrolo-[3,2-d]-and-[2,3-d]-pyrimidine Systems starting from a Common Pyrrole Derivative," *J. Chem. Soc. Perkin Transactions*, 1, 5, 483 to 487, (1978).

*Primary Examiner* — Yong Chu
*Assistant Examiner* — Michael Barker
(74) *Attorney, Agent, or Firm* — Holtz, Holtz, Goodman & Chick, PC

(57) ABSTRACT

A compound represented by the following formula (1) or a salt thereof:

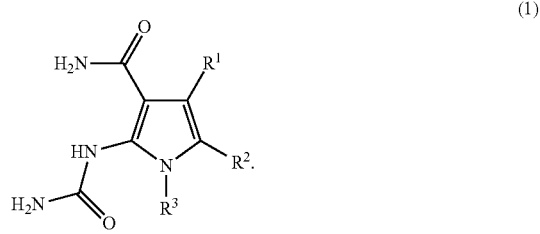

(1)

The compound has an inhibitory activity on the production of interleukin-6, and is therefore useful as a therapeutic agent for a disease associated with interleukin-6, ocular inflammatory diseases and the like. In the formula, $R^1$ represents a halogen atom, a hydrogen atom, a lower alkyl group which may have a substituent, a formyl group, or a lower alkylcarbonyl group which may have a substituent, $R^2$ represents a bicyclic hydrocarbon group which may have a substituent or a bicyclic heterocyclic group which may have a substituent, $R^3$ represents a hydrogen atom, a lower alkyl group which may have a substituent, an aryl group which may have a substituent, or an acyl group.

11 Claims, No Drawings

PYRROLE DERIVATIVE HAVING, AS SUBSTITUENTS, UREIDO GROUP, AMINOCARBONLY GROUP AND BICYCLIC GROUP WHICH MAY HAVE SUBSTITUENT

CROSS-REFERENCE TO RELATED APPLICATION

This application is the United States national phase application of International Application No. PCT/JP2009/064744 filed Aug. 25, 2009.

TECHNICAL FIELD

The present invention relates to a novel pyrrole derivative having, as substituents, a ureido group, an aminocarbonyl group, and a bicyclic group which may have a substituent or a salt thereof which is useful as a pharmaceutical. The derivative or a salt thereof has an inhibitory activity against the production of interleukin-6 (hereinafter referred to as "IL-6") and is therefore useful as a preventive and/or therapeutic agent for a disease considered to be associated with IL-6, particularly an ocular inflammatory disease.

BACKGROUND ART

IL-6 is a cytokine that was discovered as a B-cell differentiation inducing factor and has a variety of bioactivities such as antibody production system, induction of biosynthesis of acute phase protein in the liver, and acceleration of proliferation of hematopoietic stem cells based on its synergistic effect with interleukin-3.

Accordingly, if the production of IL-6 can be regulated, the prevention and/or treatment of a disease considered to be associated with IL-6 can be realized.

As the disease considered to be associated with IL-6, for example, polyclonal B cell disorders (such as intra-atrial myxoma, Castleman syndrome, rheumatoid arthritis, cervical cancer, acquired immunodeficiency syndrome and alcoholic liver cirrhosis), lymphoid tumors (such as multiple myeloma and Lennert T lymphoma), mesangioproliferative nephritis, renal cell carcinoma, psoriasis and the like have been known (Bessatsu Igaku no Ayumi (Journal of Clinical and Experimental Medicine, Supplement) Cytokines, Kiso kara Rinsho Oyo made (from Basic to Clinical Research), 28-35 (1992)).

Recently, correlation between IL-6 and ocular inflammatory diseases such as age-related macular degeneration, diabetic retinopathy and diabetic macular edema has also become known (Invest. Ophthalmol. Vis. Sci. 47, E-Abstract 905 (2006), Diabetes. Res. Clin. Pract. 61, 93-101 (2003), Ophthalmology, 110, 1690-1696 (2003)).

Further, a lot of medicinal agents for regulating IL-6 have been known. For example, it is described in WO 2003/086371 that a benzimidazole derivative having an EP4 agonistic effect inhibits IL-6 production, and MRA which is an anti-IL-6 receptor antibody is described in STN Registry files CAS No. 375823-41-9.

On the other hand, a pyrrole derivative having a ureido group as a substituent is described along with the production examples in J. Chem. Soc. Perkin Transactions 1, 5, 483-487 (1978). Further, a pyrrole derivative having an aminocarbonyl group as a substituent is described as a therapeutic agent for an immune or allergic disease in WO 2005/123671. However, a pyrrole derivative having both ureido group and aminocarbonyl group as substituents is unknown, and a pyrrole derivative having also a bicyclic group in addition to these substituents is an entirely unknown compound, and as a matter of course, the use thereof is also not known.

DISCLOSURE OF THE INVENTION

Problems that the Invention is to Solve

It is a very interesting subject to study the synthesis of a novel pyrrole derivative having, as substituents, a ureido group, an aminocarbonyl group and a bicyclic group which may have a substituent, or a salt thereof, and to find a pharmacological effect of the derivative or a salt thereof.

Means for Solving the Problems

The present inventors conducted studies of the synthesis of a novel pyrrole derivative having, as substituents, a ureido group, an aminocarbonyl group and a bicyclic group which may have a substituent, or a salt thereof, and succeeded in creating a large number of novel compounds.

Further, as a result of various studies of a pharmacological effect of the derivative or a salt thereof, the present inventors found that the derivative or a salt thereof has an inhibitory activity against IL-6 production, and thus, the present invention has been completed.

That is, the present invention relates to a compound represented by the following general formula (1) or a salt thereof (hereinafter referred to as "the present compound") and a pharmaceutical composition containing at least one compound of the present compound as an active ingredient. Further, a preferred invention for the medical use thereof relates to an inhibitor of IL-6 production containing at least one compound of the present compound as an active ingredient, or a preventive and/or therapeutic agent containing at least one compound of the present compound as an active ingredient for a disease considered to be associated with IL-6, more preferably a preventive and/or therapeutic agent containing at least one compound of the present compound as an active ingredient for an ocular inflammatory disease.

More specifically, the present invention for the pharmaceutical composition thereof relates to a preventive and/or therapeutic agent containing at least one compound of the present compound as an active ingredient for age-related macular degeneration, retinopathy of prematurity, polypoidal choroidal vasculopathy, retinal vein occlusion, diabetic retinopathy, diabetic macular edema, keratitis, conjunctivitis and uveitis, more preferably a preventive and/or therapeutic agent containing at least one compound of the present compound as an active ingredient for age-related macular degeneration, diabetic retinopathy and diabetic macular edema.

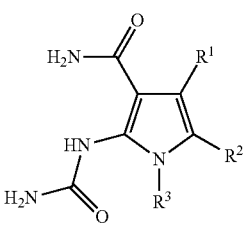

(1)

[$R^1$ represents a halogen atom, a hydrogen atom, a lower alkyl group which may have a substituent, a formyl group, or a lower alkylcarbonyl group which may have a substituent;

$R^2$ represents a bicyclic hydrocarbon group which may have a substituent or a bicyclic heterocyclic group which may have a substituent;

$R^3$ represents a hydrogen atom, a lower alkyl group which may have a substituent, an aryl group which may have a substituent, or an acyl group. The same shall apply hereinafter.]

Advantage of the Invention

The present invention provides a novel pyrrole derivative having, as substituents, a ureido group, an aminocarbonyl group, and a bicyclic group which may have a substituent or a salt thereof. The present compound has an excellent inhibitory activity against IL-6 production and is therefore useful as an inhibitor of IL-6 production, a preventive and/or therapeutic agent for a disease considered to be associated with IL-6, a preventive and/or therapeutic agent for an ocular inflammatory disease.

More specifically, the present compound is useful as a preventive and/or therapeutic agent for age-related macular degeneration, retinopathy of prematurity, polypoidal choroidal vasculopathy, retinal vein occlusion, diabetic retinopathy, diabetic macular edema, keratitis, conjunctivitis or uveitis.

BEST MODE FOR CARRYING OUT THE INVENTION

Hereinafter, definitions of terms and phrases (atoms, groups, rings and the like) to be used in this specification will be described in detail. Further, when the other definitions of terms and phrases are applied to the definitions of terms and phrases mentioned below, preferred ranges of the respective definitions and the like can also be applied.

The "halogen atom" refers to a fluorine, chlorine, bromine, or iodine atom.

The "lower alkyl group" refers to a straight-chain or branched alkyl group having 1 to 6 carbon atoms. Specific examples thereof include methyl, ethyl, n-propyl, n-butyl, n-pentyl, n-hexyl, isopropyl, isobutyl, sec-butyl, tert-butyl and isopentyl groups and the like.

The "lower alkenyl group" refers to a straight-chain or branched alkenyl group having 2 to 6 carbon atoms. Specific examples thereof include vinyl, propenyl, butenyl, pentenyl, hexenyl, ethylpropenyl and methylbutenyl groups and the like.

The "lower cycloalkyl group" refers to a cycloalkyl group having 3 to 8 carbon atoms. Specific examples thereof include cyclopropyl, cyclobutyl, cyclopentyl, cyclohexyl, cycloheptyl and cyclooctyl groups.

The "aryl group" refers to a residue formed by removing one hydrogen atom from a monocyclic aromatic hydrocarbon group, or a bicyclic or tricyclic condensed polycyclic aromatic hydrocarbon having 6 to 14 carbon atoms. Specific examples thereof include phenyl, naphthyl, anthryl and phenanthryl groups and the like.

The "lower alkoxy group" refers to a group formed by substituting the hydrogen atom of a hydroxy group with a lower alkyl group. Specific examples thereof include methoxy, ethoxy, n-propoxy, n-butoxy, n-pentyloxy, n-hexyloxy, isopropoxy, isobutoxy, sec-butoxy, tert-butoxy and isopentyloxy groups and the like.

The "lower cycloalkyloxy group" refers to a group formed by substituting the hydrogen atom of a hydroxy group with a lower cycloalkyl group. Specific examples thereof include cyclopropyloxy, cyclobutyloxy, cyclopentyloxy, cyclohexyloxy, cycloheptyloxy and cyclooctyloxy groups.

The "aryloxy group" refers to a group formed by substituting the hydrogen atom of a hydroxy group with an aryl group. Specific examples thereof include phenoxy, naphthoxy, anthryloxy and phenanthryloxy groups and the like.

The "lower alkylcarbonyl group" refers to a group formed by substituting the hydrogen atom of a formyl group with a lower alkyl group. Specific examples thereof include methylcarbonyl, ethylcarbonyl, n-propylcarbonyl, n-butylcarbonyl, n-pentylcarbonyl, n-hexylcarbonyl, isopropylcarbonyl, isobutylcarbonyl, sec-butylcarbonyl, tert-butylcarbonyl and isopentylcarbonyl groups and the like.

The "acyl group" refers to $-C(O)-R^t$.

Here, $R^t$ represents a lower alkyl group, a lower alkenyl group, a lower cycloalkyl group, an aryl group or a heterocyclic group.

The "heterocyclic ring" refers to a saturated or unsaturated monocyclic heterocyclic ring, or a bicyclic or tricyclic condensed polycyclic heterocyclic ring having one or plural heteroatoms selected from a nitrogen atom, an oxygen atom and a sulfur atom in the ring.

Specific examples of the saturated monocyclic heterocyclic ring include pyrrolidine, pyrazolidine, imidazolidine, triazolidine, piperidine, hexahydropyridazine, hexahydropyrimidine, piperazine, homopiperidine and homopiperazine rings and the like, each of which has a nitrogen atom in the ring; tetrahydrofuran and tetrahydropyran rings and the like, each of which has an oxygen atom in the ring; tetrahydrothiophene and tetrahydrothiopyran rings and the like, each of which has a sulfur atom in the ring; oxazolidine, isoxazolidine and morpholine rings and the like, each of which has a nitrogen atom and an oxygen atom in the ring; and thiazolidine, isothiazolidine and thiomorpholine rings and the like, each of which has a nitrogen atom and a sulfur atom in the ring.

Further, such a saturated monocyclic heterocyclic ring may be condensed with a benzene ring or the like to form a bicyclic or tricyclic condensed polycyclic heterocyclic ring such as a dihydroindole, dihydroindazole, dihydrobenzimidazole, tetrahydroquinoline, tetrahydroisoquinoline, tetrahydrocinnoline, tetrahydrophthalazine, tetrahydroquinazoline, tetrahydroquinoxaline, dihydrobenzofuran, dihydroisobenzofuran, chroman, isochroman, dihydrobenzothiophene, dihydroisobenzothiophene, thiochroman, isothiochroman, dihydrobenzoxazole, dihydrobenzisoxazole, dihydrobenzoxazine, dihydrobenzothiazole, dihydrobenzoisothiazole, dihydrobenzothiazine, xanthene, 4a-carbazole or perimidine ring.

Specific examples of the unsaturated monocyclic heterocyclic ring include dihydropyrrole, pyrrole, dihydropyrazole, pyrazole, dihydroimidazole, imidazole, dihydrotriazole, triazole, tetrahydropyridine, dihydropyridine, pyridine, tetrahydropyridazine, dihydropyridazine, pyridazine, tetrahydropyrimidine, dihydropyrimidine, pyrimidine, tetrahydropyrazine, dihydropyrazine, pyrazine and triazine rings and the like, each of which has a nitrogen atom in the ring; dihydrofuran, furan, dihydropyran and pyran rings and the like, each of which has an oxygen atom in the ring; dihydrothiophene, thiophene, dihydrothiopyran and thiopyran rings and the like, each of which has a sulfur atom in the ring; dihydrooxazole, oxazole, dihydroisoxazole, isoxazole, dihydrooxazine and oxazine rings and the like, each of which has a nitrogen atom and an oxygen atom in the ring; and dihydrothiazole, thiazole, dihydroisothiazole, isothiazole, dihydrothiazine and thiazine rings and the like, each of which has a nitrogen atom and a sulfur atom in the ring.

Further, such an unsaturated monocyclic heterocyclic ring may be condensed with a benzene ring or the like to form a bicyclic or tricyclic condensed polycyclic heterocyclic ring such as an indole, indazole, benzimidazole, benzotriazole, dihydroquinoline, quinoline, dihydroisoquinoline, isoquinoline, phenanthridine, dihydrocinnoline, cinnoline, dihydrophthalazine, phthalazine, dihydroquinazoline, quinazoline, dihydroquinoxaline, quinoxaline, benzofuran, isobenzofuran, chromen, isochromen, benzothiophene, isobenzothiophene, thiochromen, isothiochromen, benzoxazole, benzisoxazole, benzoxazine, benzothiazole, benzisothiazole, benzothiazine, phenoxanthine, carbazole, β-carboline, phenanthridine, acridine, phenanthroline, phenazine, phenothiazine or phenoxazine ring.

Furthermore, among the above heterocyclic rings, pyrrolidine, piperidine, piperazine, morpholine, dihydroindole, pyrrole, pyridine, pyrazine, furan, thiophene, pyran, isoxazole and thiazole rings are preferable, and pyrrolidine, piperidine, piperazine, morpholine, pyridine, pyrazine and thiophene rings are particularly preferable.

The "heterocyclic group" refers to a residue formed by removing one hydrogen atom from a heterocyclic ring.

The "heterocyclic oxy group" refers to a group formed by substituting the hydrogen atom of a hydroxy group with a heterocyclic group.

The "nitrogen-containing heterocyclic ring" refers to a ring containing one or plural nitrogen atoms in the ring among the heterocyclic rings. Specific examples thereof include pyrrolidine, piperidine, piperazine, homopiperazine, morpholine, pyrrole and pyridine rings and the like.

The "bicyclic hydrocarbon group" refers to a group formed by removing one hydrogen atom from a bicyclic hydrocarbon which is composed of 8 to 10 carbon atoms. Specific examples thereof include naphthalene, dihydronaphthalene, tetrahydronaphthalene, octatetrahydronaphthalene, indene, indane, and azulene ring groups and the like.

The "bicyclic heterocyclic group" refers to a group formed by removing one hydrogen atom from a bicyclic heterocyclic ring which is composed of one or a plurality of atoms selected from nitrogen atom, oxygen atom and sulfur atom, and 5 to 9 carbon atoms. Specific examples thereof include indole, dihydroindole, indazole, benzimidazole, quinoline, dihydroquinoline, tetrahydroquinoline, isoquinoline, phthalazine, quinazoline, quinoxaline, tetrahydroquinoxaline, benzofuran, dihydrobenzofuran, benzodioxole, dihydrobenzodioxine, benzodioxine, chromane, benzothiophene, dihydrobenzothiophene, benzoxazole, dihydrobenzoxazole, benzisoxazole, dihydrobenzoxazine, benzothiazine, dihydrobenzothiazine, benzothiazole and dihydrobenzothiazole ring groups and the like.

The "lower alkyl group which may have a substituent" and/or "lower alkylcarbonyl group which may have a substituent" refer to a "lower alkyl group" and/or a "lower alkylcarbonyl group" which may have one or plural substituents selected from the group consisting of a halogen atom, a lower cycloalkyl group, an aryl group, a heterocyclic group, a hydroxy group, a lower alkoxy group, a lower cycloalkyloxy group, an aryloxy group, a heterocyclic oxy group, a nitro group, a cyano group and —NR$^u$R$^v$.

The "aryl group which may have a substituent", "bicyclic hydrocarbon group which may have a substituent" and/or "bicyclic heterocyclic group which may have a substituent" refer to an "aryl group", a "bicyclic hydrocarbon group" and/or a "bicyclic heterocyclic group" which may have one or plural substituents selected from the group consisting of a halogen atom, a lower alkyl group, a lower cycloalkyl group, an aryl group, a heterocyclic group, a hydroxy group, a lower alkoxy group, a lower cycloalkyloxy group, an aryloxy group, a heterocyclic oxy group, a carbonyl group (an oxo group), a nitro group, a cyano group and —NR$^u$R$^v$.

Here, R$^u$ and R$^v$ are the same or different and represent a hydrogen atom, a lower alkyl group, a lower cycloalkyl group, an aryl group or a heterocyclic group, and further, R$^u$ and R$^v$ may be joined to each other to form a nitrogen-containing heterocyclic ring.

The "plural substituents" used in the present invention refers to substituents which are less than or equal to a maximum number of substitutable groups, and may be the same or different, and the number of the substituents is preferably 2 and/or 3, particularly preferably 2.

Further, the concept of the "substituent" also includes the "atom", "group" and "ring" defined above and the like.

The "inhibitor of IL-6 production" in the present invention refers to a compound which inhibits the production of IL-6 thereby to exhibit a pharmaceutical effect.

The "ocular inflammatory disease" in the present invention includes age-related macular degeneration, retinopathy of prematurity, polypoidal choroidal vasculopathy, retinal vein occlusion, diabetic retinopathy, diabetic macular edema, keratitis, conjunctivitis, uveitis and the like, and preferably age-related macular degeneration, diabetic retinopathy and diabetic macular edema.

Incidentally, the above-mentioned specific diseases are described for the purpose of understanding the invention better and are not meant to limit the scope of the invention.

The "salt" of the present compound is not particularly limited as long as it is a pharmaceutically acceptable salt, and examples thereof include salts with an inorganic acid such as hydrochloric acid, hydrobromic acid, hydroiodic acid, nitric acid, sulfuric acid or phosphoric acid; salts with an organic acid such as acetic acid, fumaric acid, maleic acid, succinic acid, citric acid, tartaric acid, adipic acid, gluconic acid, glucoheptonic acid, glucuronic acid, terephthalic acid, methanesulfonic acid, lactic acid, hippuric acid, 1,2-ethanedisulfonic acid, isethionic acid, lactobionic acid, oleic acid, pamoic acid, polygalacturonic acid, stearic acid, tannic acid, trifluoromethanesulfonic acid, benzenesulfonic acid, p-toluenesulfonic acid, lauryl sulfate, methyl sulfate, naphthalene sulfonate or sulfosalicylic acid; quaternary ammonium salts with methyl bromide, methyl iodide or the like; salts with a halogen ion such as a bromine ion, a chlorine ion or an iodine ion; salts with an alkali metal such as lithium, sodium or potassium; salts with an alkaline earth metal such as calcium or magnesium; salts with a metal such as iron or zinc; salts with ammonia; and salts with an organic amine such as triethylenediamine, 2-aminoethanol, 2,2-iminobis(ethanol), 1-deoxy-1-methylamino-2-D-sorbitol, 2-amino-2-hydroxymethyl-1,3-propanediol, procaine or N,N-bis(phenylmethyl)-1,2-ethanediamine.

In the case where there are geometric isomers or optical isomers in the present compound, these isomers are also included in the scope of the present invention.

Further, the present compound may be in the form of a hydrate or a solvate.

In the case where there is proton tautomerism in the present compound, the tautomeric isomers thereof are also included in the present invention.

In the case where there are crystalline polymorphisms and/or crystalline polymorphism groups (crystalline polymorphism systems) in the present compound, these crystalline polymorphisms and/or crystalline polymorphism groups (crystalline polymorphism systems) are also included in the present invention. Here, the crystalline polymorphism groups (crystalline polymorphism systems) mean individual crystal forms in respective stages when the crystal forms are changed by conditions for the production, crystallization, storage or the like of these crystals and/or states thereof (the states also include a formulated state) and/or all the processes thereof.

(a) Examples of the present compound include compounds in which the respective groups are as defined below and salts thereof in the compounds represented by the general formula (I) and salts thereof:

(a1) $R^1$ represents a halogen atom, a hydrogen atom, a lower alkyl group which may have a substituent, a formyl group or a lower alkylcarbonyl group which may have a substituent; and/or (a2) $R^2$ represents a bicyclic hydrocarbon group which may have a substituent or a bicyclic heterocyclic group which may have a substituent; and/or (a3) $R^3$ represents a hydrogen atom, a lower alkyl group which may have a substituent, an aryl group which may have a substituent or an acyl group.

That is, examples of the present compound include, in the compounds represented by the general formula (1), compounds which comprise one or a combination of two or more selected from the above (a1), (a2) and (a3), and salts thereof.

(b) Preferred examples of the present compound include compounds in which the respective groups are as defined below and salts thereof in the compounds represented by the general formula (1) and salts thereof:

(b1) $R^1$ represents a halogen atom or a hydrogen atom; and/or (b2) $R^2$ represents a bicyclic hydrocarbon group which may have a substituent or a bicyclic heterocyclic group which may have a substituent; and/or (b3) $R^3$ represents a hydrogen atom.

That is, preferred examples of the present compound include, in the compounds represented by the general formula (1), compounds which comprise one or a combination of two or more selected from the above (b1), (b2) and/or (b3), and salts thereof. Further, the selected conditions can be combined with the above conditions (a).

(c) Preferred examples of the bicyclic hydrocarbon group in the present compound include naphthalene or tetrahydronaphthalene ring. Further, the selected conditions can be combined with the above conditions (a) and/or (b).

(d) Preferred examples of the bicyclic heterocyclic group in the present compound include indole, benzofuran, dihydrobenzofuran, benzodioxole, dihydrobenzodioxine, benzothiophene, benzoxazine, benzothiazole or benzothiazine ring. Further, the selected conditions can be combined with the above conditions (a) and/or (b).

(e) Particularly preferred specific examples of the present compound include the following compounds and salts thereof.

2-Aminocarbonylamino-5-(2-naphthyl)pyrrole-3-carboxamide,
2-Aminocarbonylamino-5-(benzofuran-2-yl)pyrrole-3-carboxamide,
2-Aminocarbonylamino-5-(benzothiophen-5-yl)pyrrole-3-carboxamide,
2-Aminocarbonylamino-5-(benzofuran-5-yl)pyrrole-3-carboxamide,
2-Aminocarbonylamino-5-(2,3-dihydro-1,4-benzodioxin-5-yl)pyrrole-3-carboxamide,
2-Aminocarbonylamino-5-(3-methylbenzothiophen-2-yl)pyrrole-3-carboxamide, and
2-Aminocarbonylamino-5-(2,3-dihydrobenzofuran-7-yl)pyrrole-3-carboxamide.

The present compounds can be prepared according to the following methods. Each specific process for preparing the present compounds is described in detail in the following examples (section of "Production Examples"). The term "Hal" used in the following synthetic routes represents a halogen atom.

The processes for preparing the present compounds are divided roughly into the methods described bellow, and the suitable method can be chosen according to the kind of substituent.

The present compound (I) can be synthesized according to synthetic route 1. Namely, the present compound (I) can be given by the reaction of compound (II) with trichloroacetyl isocyanate in an organic solvent such as tetrahydrofuran (hereinafter referred to as "THF") or N,N-dimethylformamide (hereinafter referred to as "DMF") at −80° C. to room temperature for 1 hour to 3 hours, followed by the reaction with ammonia in methanol solution at 0° C. to room temperature for 1 hour to 72 hours.

Synthetic Route 1

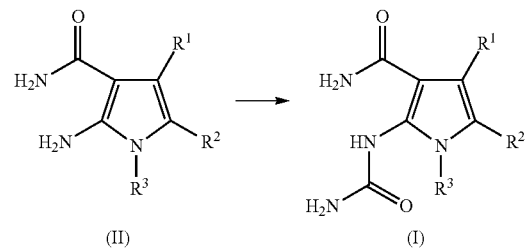

The compound (II)-(a) can be synthesized according to synthetic route 2-1. Namely, the compound (IV) can be given by the treatment of compound (III) in an organic solvent such as dichloromethane or THF in the presence of a halogenating reagent such as phenyltrimethylammonium tribromide, or N-bromosuccinimide at 0° C. to 60° C. for 1 hour to 24 hours. The compound (II)-(a) can be given by the reaction of the obtainable compound (IV) with malonamamidine (V) in an organic solvent such as ethanol or DMF in the presence of a base such as sodium ethoxide or potassium carbonate at 0° C. to 80° C. for 1 hour to 48 hours.

Synthetic Route 2-1

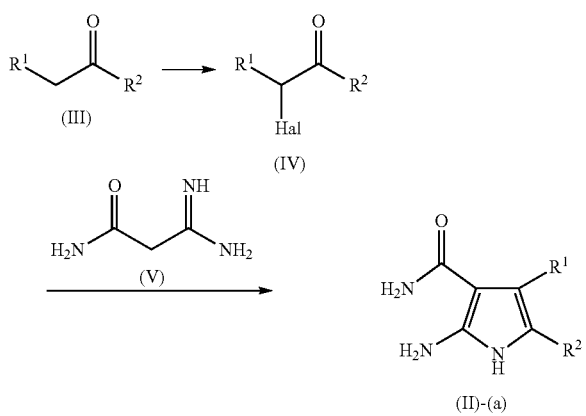

The compound (II)-(b) can be synthesized according to synthetic route 2-2. Namely, the compound (II)-(b) can be given by the reaction of compound (II)-(c) with an alkyl halide or aryl halide (VI) in an organic solvent such as THF or DMF in the presence of a base such as sodium hydroxide or sodium hydride at 0° C. to 100° C. for 1 hour to 24 hours.

Synthetic Route 2-2

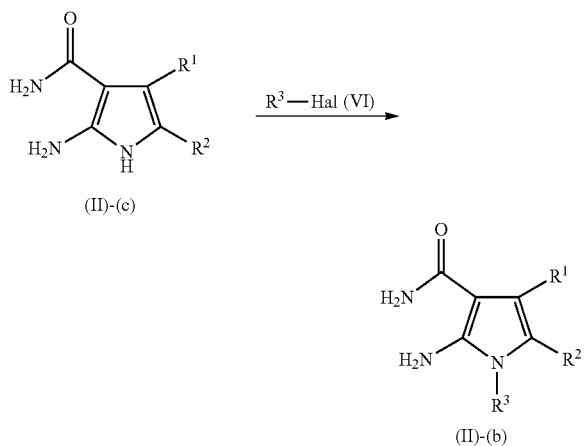

The compound (I)-(a) can be synthesized according to synthetic route 3. Namely, the compound (I)-(a) can be given by the treatment of compound (I)-(b) in an organic solvent such as dichloromethane or DMF in the presence of a halogenating reagent such as N-chlorosuccinimide or N-bromosuccinimide at room temperature to 80° C. for 1 hour to 24 hours.

Synthetic Route 3

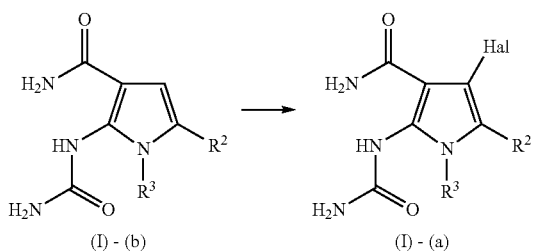

The present compound prepared by the above synthetic routes can also be converted into the above-mentioned salt, hydrate or solvate using widely used techniques.

Further, the details will be described in the following Examples (Pharmacological Tests). The inhibitory effect of the present compound on TNF-α-induced IL-6 production was studied using normal human skin fibroblast-derived CCD-1059Sk cells. As a result, the present compound exhibited an excellent inhibitory activity against IL-6 production. Therefore, the present compound is useful as an IL-6 inhibitor. Furthermore, as mentioned above, IL-6 relates to various diseases, therefore the present compound having an inhibitory activity against IL-6 production is useful as a preventive and/or therapeutic agent for the disease considered to be associated with IL-6.

Specifically, the present compound is useful as a preventive and/or therapeutic agent for ocular inflammatory diseases, more specifically useful as a preventive and/or therapeutic agent for age-related macular degeneration, retinopathy of prematurity, polypoidal choroidal vasculopathy, retinal vein occlusion, diabetic retinopathy, diabetic macular edema, keratitis, conjunctivitis and uveitis.

The present compound can be administered orally or parenterally. Examples of the mode of administration include oral administration, ophthalmic topical administration (such as eye drop administration, instillation in the conjunctival sac, intravitreal administration, subconjunctival administration and sub-Tenon's administration), intravenous administration and transdermal administration, and the present compound can be formulated into a preparation suitable for such an administration mode by properly selecting and using a pharmaceutically acceptable additive as needed.

Examples of the dosage form include a tablet, a capsule, a granule, a powder and the like in the case of an oral preparation, and an injection, an eye drop, an eye ointment, an insert, an intraocular implant and the like in the case of a parenteral preparation.

For example, in the case of a tablet, a capsule, a granule, a powder or the like, such a preparation can be prepared by properly selecting and using an excipient such as lactose, glucose, D-mannitol, anhydrous calcium hydrogen phosphate, starch or sucrose; a disintegrant such as carboxymethyl cellulose, calcium carboxymethyl cellulose, croscarmellose sodium, crosspovidone, starch, partially gelatinized starch or low-substituted hydroxypropyl cellulose; a binder such as hydroxypropyl cellulose, ethyl cellulose, gum arabic, starch, partially gelatinized starch, polyvinylpyrrolidone or polyvinyl alcohol; a lubricant such as magnesium stearate, calcium stearate, talc, hydrous silicon dioxide or a hydrogenated oil; a coating agent such as purified sucrose, hydroxypropylmethyl cellulose, hydroxypropyl cellulose, methyl cellulose, ethyl cellulose or polyvinylpyrrolidone; a corrigent such as citric acid, aspartame, ascorbic acid or menthol; or the like as needed.

An injection can be prepared by properly selecting and using a tonicity agent such as sodium chloride; a buffer such as sodium phosphate; a surfactant such as polyoxyethylene sorbitan monoolate; a viscosity-increasing agent such as methyl cellulose; or the like as needed.

An eye drop can be prepared by properly selecting and using a tonicity agent such as sodium chloride or concentrated glycerin; a buffer such as sodium phosphate or sodium acetate; a surfactant such as polyoxyethylene sorbitan monoolate, polyoxyl 40 stearate or polyoxyethylene hydrogenated castor oil; a stabilizer such as sodium citrate or sodium edetate; a preservative such as benzalkonium chloride or paraben; or the like as needed. The pH of the eye drop is permitted as long as it falls within the range that is acceptable as an ophthalmic preparation, is preferably in the range of from 4 to 8.

An eye ointment can be prepared using a widely used base such as white petrolatum or liquid paraffin.

An insert can be prepared using a biodegradable polymer such as hydroxypropyl cellulose, hydroxypropylmethyl cellulose, a carboxy vinyl polymer or polyacrylic acid, and if necessary, an excipient, a binder, a stabilizer, a pH adjusting agent or the like can be properly selected and used as appropriate.

A preparation for intraocular implant can be prepared using a biodegradable polymer such as polylactic acid, polyglycolic acid, a lactic acid-glycolic acid copolymer or hydroxypropyl cellulose, and if necessary, an excipient, a binder, a stabilizer, a pH adjusting agent or the like can be properly selected and used as appropriate.

The dose of the present compound can be properly selected depending on the dosage form, symptoms, age, body weight of a patient or the like. For example, in the case of oral administration, it can be administered in an amount of from 0.01 to 5000 mg, preferably from 0.1 to 2500 mg, particularly preferably from 0.5 to 1000 mg per day in a single dose or several divided doses. In the case of an injection, it can be administered in an amount of from 0.00001 to 2000 mg, preferably from 0.0001 to 1500 mg, particularly preferably from 0.001 to 500 mg per day in a single dose or several divided doses. In the case of an eye drop, a preparation containing the present compound at a concentration of from 0.00001 to 10% (w/v), preferably from 0.0001 to 5% (w/v), particularly preferably from 0.001 to 1% (w/v) can be instilled into the eye once or several times a day. In the case of an eye ointment, a preparation containing the present compound in an amount of from 0.0001 to 2000 mg can be applied. In the case of an insert or a preparation for intraocular implant, a preparation containing the present compound in an amount of from 0.0001 to 2000 mg can be inserted or implanted.

Hereinafter, Production Examples of the present compound, Preparation Examples and results of pharmacological tests will be described. However, these examples are described for the purpose of understanding the invention better and are not meant to limit the scope of the invention.

PRODUCTION EXAMPLES

Reference Example 1-1

2-Amino-5-(2-naphthyl)pyrrole-3-carboxamide (Reference Compound No. 1-1)

Under ice-cooling, sodium ethoxide (2.7 g, 40 mmol) was added to a suspension of malonamamidine hydrochloride (5.5 g, 40 mmol) in dehydrated ethanol (130 mL), and then the mixture was stirred for 20 minutes. 2-Bromoacetylnaphthalene (5.0 g, 20 mmol) was added thereto, and the whole was stirred at room temperature overnight. The reaction mixture was concentrated in vacuo, and the obtained residue was purified by silica gel column chromatography to give the title reference compound (1.5 g) as a black solid (Yield 30%).

Reference Example 1-2

2-Amino-5-(7-methoxybenzofuran-2-yl)pyrrole-3-carboxamide (Reference Compound No. 1-2)

Phenylrimethylammonium tribromide (2.0 g, 5.3 mmol) was added to a solution of 2-acetyl-7-methoxybenzofuran (1.0 g, 5.3 mmol) in anhydrous tetrahydrofuran (25 mL), and the mixture was stirred at room temperature for 4 hours. After the insoluble solid was filtered out, the filtrate was concentrated in vacuo to give a mixture including 2-bromoacetyl-7-methoxybenzofuran. Malonamamidine hydrochloride (1.5 g, 11 mmol) and potassium carbonate (1.5 g, 11 mmol) were added to a solution of this mixture in anhydrous N,N-dimethylformamide (40 mL) and the whole was stirred at 60° C. overnight. After cooling, the reaction mixture was diluted with water (200 mL), and the whole was extracted with ethyl acetate (100 mL, twice). The organic layer was washed with brine (100 mL) and dried over anhydrous magnesium sulfate. The solvent was removed in vacuo, and the obtained residue was purified by silica gel column chromatography to give the title reference compound (0.33 g) as a dark green solid (Yield 23%).

| 2-Amino-5-(2-naphthyl)pyrrole-3-carboxamide (Reference compound No. 1-1) | $^1$H-NMR (500 MHz, DMSO-$d_6$) d 5.77(s, 2H), 6.86(d, J = 2.7 Hz, 1H), 7.37(m, 1H), 7.45(m, 1H), 7.61(dd, J = 8.7, 1.7 Hz, 1H), 7.75(d, J = 7.9 Hz, 1H), 7.77-7.84(m, 3H), 10.78(s, 1H) |
|---|---|
| 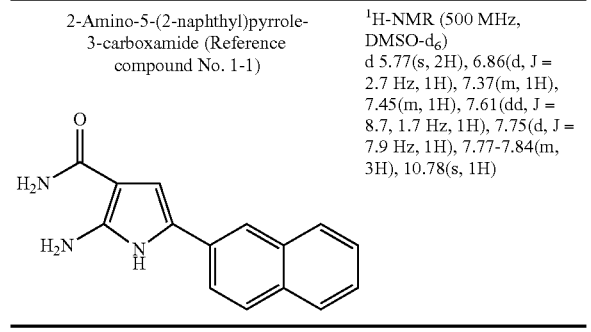 | |

| 2-Amino-5-(7-methoxybenzofuran-2-yl)pyrrole-3-carboxamide (Reference compound No. 1-2) | $^1$H-NMR (400 MHz, DMSO-$d_6$) d 3.93(s, 3H), 5.91(s, 2H), 6.68(s, 1H), 6.82(m, 1H), 6.87(d, J = 2.4 Hz, 1H), 7.05-7.13(m, 2H), 10.84(s, 1H) |
|---|---|
| 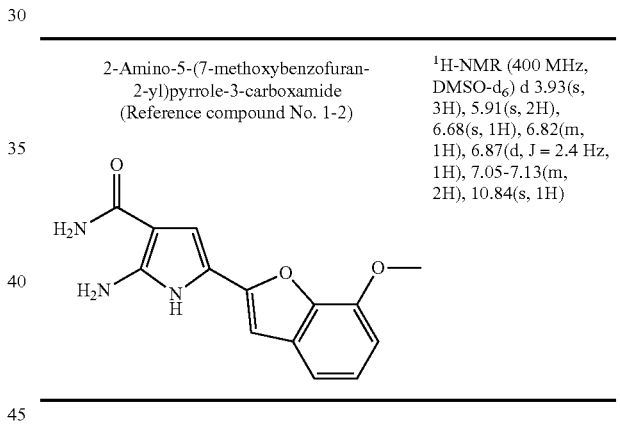 | |

As described below, using commercially available compounds and reference compounds selected from No. 3-1 and 6-1, Reference compounds No. 1-3 to 1-20 were obtained by a method similar to that of Reference compound No. 1-1 or 1-2.

| 2-Amino-5-(benzothiophen-3-yl)pyrrole-3-carboxamide (Reference compound No. 1-3) | $^1$H-NMR (400 MHz, DMSO-$d_6$) d 5.75(s, 2H), 6.90(d, J = 2.7 Hz, 1H), 7.39-7.50(m, 2H), 7.53(s, 1H), 8.00(m, 1H), 8.24(d, J = 7.6 Hz, 1H), 10.59 (s, 1H) |
|---|---|
| 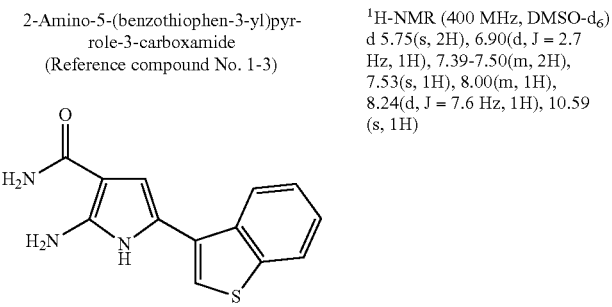 | |

| | | |
|---|---|---|
| 2-Amino-5-(benzothiophen-2-yl)pyrrole-3-carboxamide (Reference compound No. 1-4) 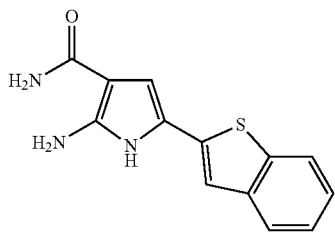 | $^1$H-NMR (400 MHz, DMSO-d$_6$) d 5.90(s, 2H), 6.67(d, J = 2.4 Hz, 1H), 7.20(td, J = 7.6, 1.1 Hz, 1H), 7.25(s, 1H), 7.29 (td, J = 7.6, 1.1 Hz, 1H), 7.65 (d, J = 7.6 Hz, 1H), 7.81(d, J = 7.6 Hz, 1H), 10.88(s, 1H) | |
| 2-Amino-5-(benzofuran-2-yl)pyrrole-3-carboxamide (Reference compound No. 1-5) 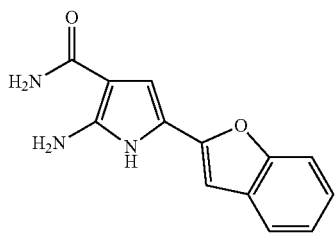 | $^1$H-NMR (500 MHz, DMSO-d$_6$) d 5.93(s, 2H), 6.71(s, 1H), 6.85(d, J = 2.4 Hz, 1H), 7.13-7.20(m, 2H), 7.45(m, 1H), 7.52(m, 1H), 10.87(s, 1H) | |
| 2-Amino-5-(benzothiophen-5-yl)pyrrole-3-carboxamide (Reference compound No. 1-6) 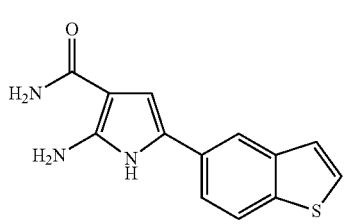 | $^1$H-NMR (400 MHz, DMSO-d$_6$) d 5.68(s, 2H), 6.74(d, J = 2.7 Hz, 1H), 7.39(d, J = 5.5 Hz, 1H), 7.45(dd, J = 8.5, 1.7 Hz, 1H), 7.73(d, J = 5.5 Hz, 1H), 7.87(d, J = 1.7 Hz, 1H), 7.90 (d, J = 8.5 Hz, 1H), 10.69(s, 1H) | |
| 2-Amino-5-(5-bromo-2,3-dihydrobenzofuran-7-yl)pyrrole-3-carboxamide (Reference compound No. 1-7) 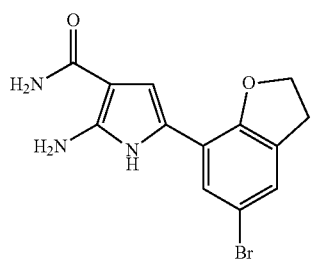 | $^1$H-NMR (400 MHz, DMSO-d$_6$) d 3.20(t, J = 8.8 Hz, 2H), 4.65 (t, J = 8.8 Hz, 2H), 5.81(s, 2H), 6.83(d, J = 2.7 Hz, 1H), 7.08(d, J = 2.1 Hz, 1H), 7.37 (d, J = 2.1 Hz, 1H), 10.30(s, 1H) | |

| Compound | NMR |
|---|---|
| 2-Amino-5-(benzofuran-5-yl)pyrrole-3-carboxamide (Reference compound No. 1-8) 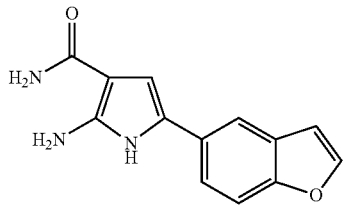 | $^1$H-NMR (400 MHz, DMSO-$d_6$) δ 5.64(s, 2H), 6.56(br s, 2H), 6.64(d, J = 2.7 Hz, 1H), 6.93 (dd, J = 2.2, 1.0 Hz, 1H), 7.38 (dd, J = 8.5, 1.8 Hz, 1H), 7.53 (d, J = 8.5 Hz, 1H), 7.65(d, J = 1.8 Hz, 1H), 7.95(d, J = 2.2 Hz, 1H), 10.62(s, 1H) |
| 2-Amino-5-(5,5,8,8-tetramethyl-5,6,7,8-tetrahydronaphthalen-2-yl)pyrrole-3-carboxamide (Reference compound No. 1-9) 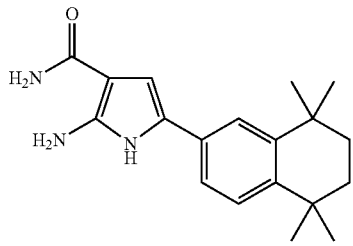 | $^1$H-NMR (400 MHz, DMSO-$d_6$) δ 1.22(s, 6H), 1.27(s, 6H), 1.63(s, 4H), 5.62(s, 2H), 6.62(d, J = 2.7 Hz, 1H), 7.16 (dd, J = 8.3, 1.7 Hz, 1H), 7.22 (d, J = 8.3 Hz, 1H), 7.36(d, J = 1.7 Hz, 1H), 10.53(s, 1H) |
| 2-Amino-5-(2,3-dihydro-1,4-benzodioxin-6-yl)pyrrole-3-carboxamide (Reference compound No. 1-10) 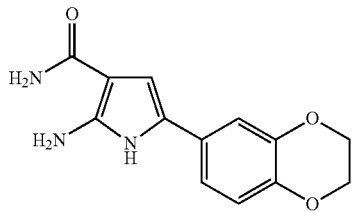 | $^1$H-NMR (400 MHz, DMSO-$d_6$) δ 4.14-4.29(m, 4H), 5.59(s, 2H), 6.51(d, J = 2.7 Hz, 1H), 6.79(d, J = 8.5 Hz, 1H), 6.88 (dd, J = 8.5, 2.0 Hz, 1H), 6.91 (d, J = 2.0 Hz, 1H), 10.47(s, 1H) |
| 2-Amino-5-(1,3-benzodioxol-5-yl)pyrrole-3-carboxamide (Reference compound No. 1-11) 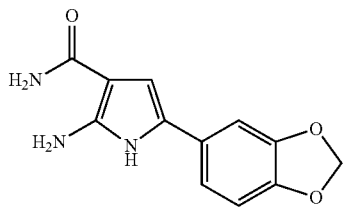 | $^1$H-NMR (400 MHz, DMSO-$d_6$) δ 5.61(s, 2H), 5.98(s, 2H), 6.54(d, J = 2.7 Hz, 1H), 6.86-6.90(m, 2H), 6.96(d, J = 1.0 Hz, 1H), 10.48(s, 1H) |

| | |
|---|---|
| 2-Amino-5-(5-chloro-2,2-dimethyl-2,3-dihydrobenzofuran-7-yl)pyrrole-3-carboxamide (Reference compound No. 1-12) 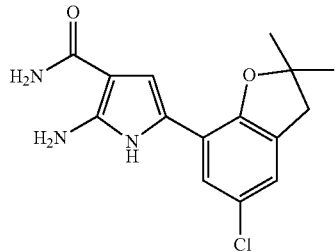 | $^1$H-NMR (500 MHz, DMSO-$d_6$) d 1.48(s, 6H), 3.00(s, 2H), 5.84(s, 2H), 6.83(d, J = 2.4 Hz, 1H), 6.91(d, J = 2.1 Hz, 1H), 7.22(d, J = 2.4 Hz, 1H), 10.16 (s, 1H) |
| 2-Amino-5-(3,5-dimethylbenzothiophen-2-yl)pyrrole-3-carboxamide (Reference compound No. 1-13) 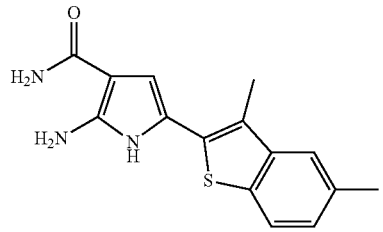 | $^1$H-NMR (400 MHz, DMSO-$d_6$) d 2.41(s, 3H), 2.43(s, 3H), 5.75(s, 2H), 6.63(d, J = 2.9 Hz, 1H), 7.10(dd, J = 8.0, 1.2 Hz, 1H), 7.48(s, 1H), 7.72(d, J = 8.0 Hz, 1H), 10.35(s, 1H) |
| 2-Amino-5-(3-methylbenzothiophen-2-yl)pyrrole-3-carboxamide (Reference compound No. 1-14) 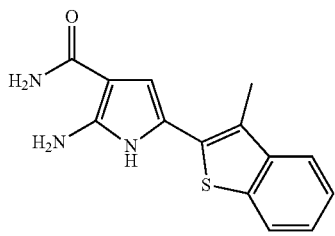 | $^1$H-NMR (400 MHz, DMSO-$d_6$) d 2.43(s, 3H), 5.76(s, 2H), 6.65(d, J = 2.7 Hz, 1H), 7.27 (m, 1H), 7.37(m, 1H), 7.68(d, J = 7.6 Hz, 1H), 7.85(d, J = 7.6 Hz, 1H), 10.38(s, 1H) |
| 2-Amino-5-(2,3-dihydro-1,4-benzodioxin-5-yl)pyrrole-3-carboxamide (Reference compound No. 1-15) 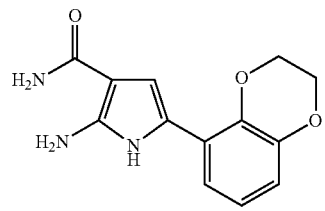 | $^1$H-NMR (400 MHz, DMSO-$d_6$) d 4.24-4.28(m, 2H), 4.31-4.36 (m, 2H), 5.70(s, 2H), 6.57 (dd, J = 7.8, 1.5 Hz, 1H)., 6.73-6.79(m, 2H), 6.96(dd, J = 7.8, 1.5 Hz, 1H), 10.11(s, 1H) |

| | |
|---|---|
| 2-Amino-5-(5-chloro-2,3-dihydro-benzofuran-7-yl)pyrrole-3-carboxamide (Reference compound No. 1-16)<br>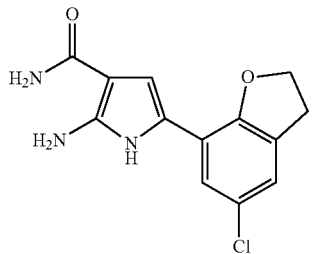 | $^1$H-NMR (400 MHz, DMSO-d$_6$) d 3.19(t, J = 8.8 Hz, 2H), 4.65 (t, J = 8.8 Hz, 2H), 5.81(s, 2H), 6.84(d, J = 2.7 Hz, 1H), 6.96(d, J = 2.2 Hz, 1H), 7.24 (d, J = 2.2 Hz, 1H), 10.30(s, 1H) |
| 2-Amino-5-(1,3-benzothiazol-2-yl)pyrrole-3-carboxamide (Reference compound No. 1-17)<br>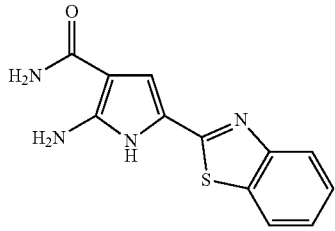 | $^1$H-NMR (500 MHz, DMSO-d$_6$) d 5.98(s, 2H), 7.19(d, J = 2.4 Hz, 1H), 7.28(t, J = 7.9 Hz, 1H), 7.41(t, J = 7.9 Hz, 1H), 7.76(d, J = 7.9 Hz, 1H), 7.95 (d, J = 7.9 Hz, 1H), 11.10(s, 1H) |
| 2-Amino-5-(3-oxo-3,4-dihydro-2H-1,4-benzoxazin-6-yl)pyrrole-3-carboxamide (Reference compound No. 1-18)<br>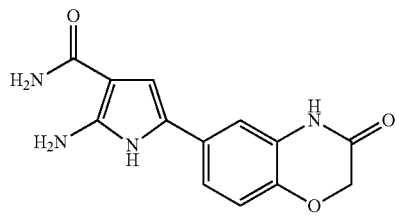 | $^1$H-NMR (400 MHz, DMSO-d$_6$) d 4.53(s, 2H), 5.63(s, 2H), 6.49(d, J = 2.7 Hz, 1H), 6.90 (d, J = 8.3 Hz, 1H), 6.90(d, J = 2.0 Hz, 1H), 6.96(dd, J = 8.3, 2.0 Hz, 1H), 10.48(s, 1H), 10.79(s, 1H) |
| 2-Amino-5-(3-oxo-3,4-dihydro-2H-1,4-benzothiazin-6-yl)pyrrole-3-carboxamide (Reference compound No. 1-19)<br>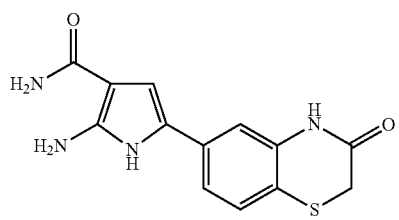 | $^1$H-NMR (400 MHz, DMSO-d$_6$) d 3.44(s, 2H), 5.70(s, 2H), 6.60(d, J = 2.9 Hz, 1H), 6.97 (d, J = 2.0 Hz, 1H), 7.02(dd, J = 8.2, 2.0 Hz, 1H), 7.24(d, J = 8.2 Hz, 1H), 10.54(s, 1H), 10.60(s, 1H) |

-continued

| 2-Amino-5-(indol-6-yl)pyrrole-3-carboxamide (Reference compound No. 1-20) 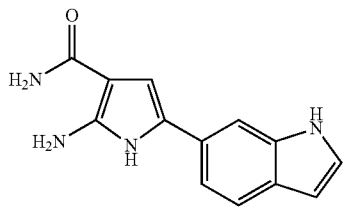 | ¹H-NMR (400 MHz, DMSO-d₆) d 5.59(s, 2H), 6.35(m, 1H), 6.58(d, J = 2.7 Hz, 1H), 7.12 (dd, J = 8.3, 1.5 Hz, 1H), 7.25 (dd, J = 2.9, 2.4 Hz, 1H), 7.40 (s, 1H), 7.45(d, J = 8.3 Hz, 1H), 10.52(s, 1H), 11.02(s, 1H) |

Reference Example 2

5'-Chloro-2'-(2-methyl-2-propenyloxy)acetophenone (Reference Compound No. 2-1)

A suspension of 5'-chloro-2'-hydroxyacetophenone (0.86 g, 5.0 mmol), potassium carbonate (1.4 g, 10 mmol) and 3-bromo-2-methylpropene (0.56 mL, 5.5 mmol) in anhydrous N,N-dimethylformamide (20 mL) was stirred at 60° C. for 4 hours. After cooling, the reaction mixture was diluted with water (100 mL), and the whole was extracted with ethyl acetate (100 mL). The organic layer was washed with saturated aqueous ammonium chloride solution (50 mL) and brine (50 mL) and dried over anhydrous magnesium sulfate. The solvent was removed in vacuo to give the title reference compound (1.1 g) as orange oil (Yield 96%).

| 5'-Chloro-2'-(2-methyl-2-propenyloxy)acetophenone (Reference compound No. 2-1) 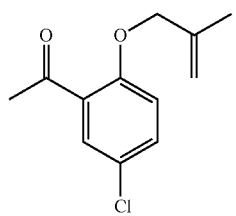 | ¹H-NMR (500 MHz, CDCl₃) d 1.85(s, 3H), 2.63(s, 3H), 4.52(s, 2H), 5.05(t, J = 1.1 Hz, 1H), 5.10(t, J = 1.1 Hz, 1H), 6.89(d, J = 8.9 Hz, 1H), 7.37(dd, J = 8.9, 2.7 Hz, 1H), 7.70(d, J = 2.7 Hz, 1H) |

Reference Example 3

7-Acetyl-5-chloro-2,2-dimethyl-2,3-dihydrobenzofuran (Reference Compound No. 3-1)

Aluminum chloride (6.0 g, 45 mmol) was added to a solution of 5-chloro-2-(2-methyl-2-propenyloxy)acetophenone (Reference compound No. 2-1, 6.6 g, 29 mmol) in anhydrous dichloromethane (200 mL) at −70° C. and the mixture was stirred for 1 hour. The temperature was raised to −40° C. slowly and the mixture was stirred for 1 hour. Water (200 mL) was added to the reaction mixture, the whole was extracted with chloroform (100 mL), and the organic layer was dried over anhydrous magnesium sulfate. The solvent was removed in vacuo, and the residue was purified by silica gel column chromatography to give the title reference compound (1.1 g) as a colorless solid (Yield 17%).

| 7-Acetyl-5-chloro-2,2-dimethyl-2,3-dihydrobenzofuran (Reference compound No. 3-1) 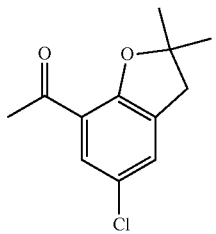 | ¹H-NMR (400 MHz, CDCl₃) d 1.53(s, 3H), 1.56(s, 3H), 2.59(s, 3H), 3.02(s, 2H), 7.24(m, 1H), 7.66(m, 1H) |

Reference Example 4

3'-Bromo-2'-(2-bromoethoxy)-5'-chloroacetophenone (Reference Compound No. 4-1)

A suspension of 3'-bromo-5'-chloro-2'-hydroxyacetophenone (2.4 g, 10 mmol), potassium carbonate (2.8 g, 20 mmol) and 1,2-dibromoethane (3.5 mL, 41 mmol) in anhydrous N,N-dimethylformamide (30 mL) was stirred at 50° C. overnight. After cooling, the reaction mixture was diluted with water (100 mL), and the whole was extracted with ethyl acetate (100 mL). The organic layer was washed with saturated aqueous ammonium chloride solution (50 mL, twice) and brine (50 mL) and dried over anhydrous magnesium sulfate. The solvent was removed in vacuo to give the title reference compound (4.4 g) as orange oil (Quantitative).

| 3'-Bromo-2'-(2-bromoethoxy)-5'-chloroacetophenone (Reference compound No. 4-1) 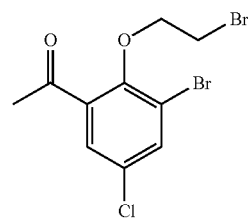 | ¹H-NMR (400 MHz, CDCl₃) d 2.64(s, 3H), 3.68(t, J = 6.2 Hz, 2H), 4.26(t, J = 6.2 Hz, 2H), 7.48(d, J = 2.4 Hz, 1H), 7.69(d, J = 2.4 Hz, 1H) |

Reference Example 5

2-[3-Bromo-2-(2-bromoethoxy)-5-chlorophenyl]-2,5,5-trimethyl-1,3-dioxane (Reference Compound No. 5-1)

A solution of 3'-bromo-2'-(2-bromoethoxy)-5'-chloroacetophenone (Reference compound No. 4-1, 4.4 g, 10 mmol), neopentylglycol (1.2 g, 1.2 mmol) and p-toluenesulfonic acid monohydrate (0.22 g, 12 mmol) in anhydrous toluene (50 mL) was refluxed overnight. After cooling, ethyl acetate (50 mL) and saturated aqueous sodium hydrogen carbonate solution (100 mL) were added to the reaction mixture and the whole was partitioned. The organic layer was washed with brine (50 mL) and dried over anhydrous magnesium sulfate. The solvent was removed in vacuo and the residue was purified by silica gel column chromatography to give the title reference compound (2.8 g) as a pale yellow oil (Yield 63%).

| 2-[3-Bromo-2-(2-bromoethoxy)-5-chlorophenyl]-2,5,5-trimethyl-1,3-dioxane (Reference compound No. 5-1) 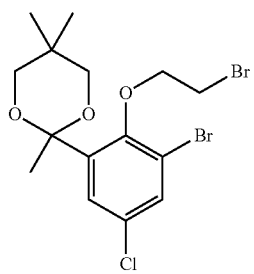 | $^1$H-NMR (400 MHz, CDCl$_3$) d 0.73(s, 3H), 1.20(s, 3H), 1.65(s, 3H), 3.40(d, J = 11.1 Hz, 2H), 3.50(d, J = 11.1 Hz, 2H), 3.70(t, J = 6.8 Hz, 2H), 4.22(t, J = 6.8 Hz, 2H), 7.44 (d, J = 2.7 Hz, 1H), 7.54(d, J = 2.7 Hz, 1H) |
|---|---|

Reference Example 6

7-Acetyl-5-chloro-2,3-dihydrobenzofuran (Reference Compound No. 6-1)

1.6 M n-Butyllithium in hexane solution (4.7 mL, 7.6 mmol) was added dropwise to a solution of 2-[3-bromo-2-(2-bromoethoxy)-5-chlorophenyl]-2,5,5-trimethyl-1,3-dioxane (Reference compound No. 5-1, 2.8 g, 6.3 mmol) in anhydrous tetrahydrofuran (30 mL) over 5 minutes at −70° C. and the whole was stirred for 1.5 hours. The whole was stirred under ice cooling for 1 hour and at room temperature overnight. The reaction mixture was diluted with water (50 mL) and extracted with ethyl acetate (50 mL). The organic layer was washed with saturated aqueous ammonium chloride solution (50 mL), saturated aqueous sodium hydrogen carbonate solution (50 mL), and brine (50 mL), and then dried over anhydrous magnesium sulfate. The solvent was removed in vacuo and tetrahydrofuran (30 mL), methanol (5 mL) and 1N aqueous hydrogen chloride solution (30 mL) were added to the residue, and the whole was stirred at room temperature for 5 hours. The reaction mixture was diluted with water (50 mL) and extracted with ethyl acetate (50 mL). The organic layer was washed with saturated aqueous sodium hydrogen carbonate solution (50 mL) and brine (50 mL), and then dried over anhydrous magnesium sulfate. The solvent was removed in vacuo and the obtained solid was filtered off with hexane (10 mL) to give the title reference compound (0.31 g) as a pale yellow solid (Yield 25%).

| 7-Acetyl-5-chloro-2,3-dihydrobenzofuran (Reference compound No. 6-1) 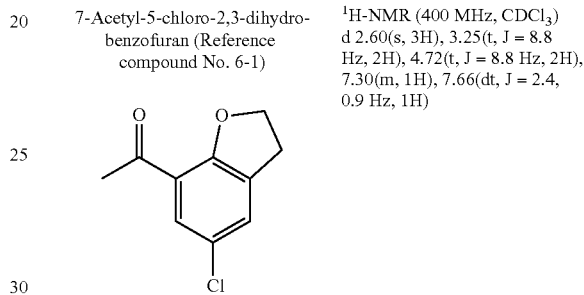 | $^1$H-NMR (400 MHz, CDCl$_3$) d 2.60(s, 3H), 3.25(t, J = 8.8 Hz, 2H), 4.72(t, J = 8.8 Hz, 2H), 7.30(m, 1H), 7.66(dt, J = 2.4, 0.9 Hz, 1H) |
|---|---|

Example 1

2-Aminocarbonylamino-5-(2-naphthyl)pyrrole-3-carboxamide (Compound No. 1-1)

Trichloroacetyl isocyanate (470 μL, 4.0 mmol) was added dropwise to a solution of 2-amino-5-(2-naphthyl)pyrrole-3-carboxamide (Reference compound No. 1-1, 1.0 g, 4.0 mmol) in anhydrous tetrahydrofuran (20 mL) at −30° C. over 5 minutes, and the whole was stirred for 1.5 hours. Furthermore, 2.0 M ammonia solution in methanol (20 mL, 40 mmol) was added thereto, and the whole was stirred at room temperature for 3 days. The precipitated solid was filtered off and washed with a mixed solvent of diethylether-ethanol (3:1) (20 mL). The obtained solid was dried at 40° C. under reduced pressure to give the target compound (0.67 g) as a pale gray solid (Yield 58%).

| 2-Aminocarbonylamino-5-(2-naphthyl)pyrrole-3-carboxamide (Compound No. 1-1) 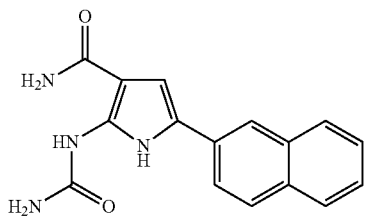 | $^1$H-NMR (500 MHz, DMSO-d$_6$) d 6.87(br s, 3H), 7.03(d, J = 3.1 Hz, 1H), 7.35(br s, 1H), 7.42(m, 1H), 7.49(m, 1H), 7.63(dd, J = 8.7, 1.7 Hz, 1H), 7.84(d, J = 7.9 Hz, 1H), 7.86-7.94(m, 3H), 9.70(s, 1H), 11.29(s, 1H) |
|---|---|

As described below, using reference compounds selected from No. 1-2 to 1-20, Compounds No. 1-2 to 1-20 were obtained by a method similar to that of Compound No. 1-1.

| | |
|---|---|
| 2-Aminocarbonylamino-5-(7-methoxybenzofuran-2-yl)pyrrole-3-carboxamide (Compound No. 1-2) 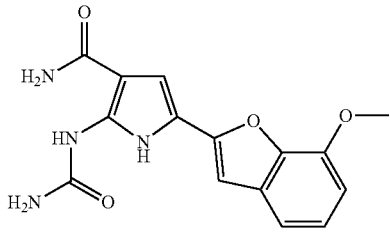 | $^1$H-NMR (500 MHz, DMSO-$d_6$) d 3.94(s, 3H), 6.89(br s, 4H), 7.00(s, 1H), 7.04(d, J = 2.7 Hz, 1H), 7.08-7.13(m, 3H), 9.76(s, 1H), 11.28(s, 1H). |
| 2-Aminocarbonylamino-5-(benzothiophen-3-yl)pyrrole-3-carboxamide (Compound No. 1-3) 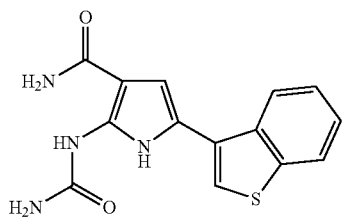 | $^1$H-NMR (500 MHz, DMSO-$d_6$) d 6.83(br s, 3H), 7.02(d, J = 3.1 Hz, 1H), 7.41-7.52(m, 3H), 7.77(s, 1H), 8.03(d, J = 7.9 Hz, 1H), 8.19(d, J = 7.9 Hz, 1H), 9.70(s, 1H), 11.11(s, 1H) |
| 2-Aminocarbonylamino-5-(benzothiophen-2-yl)pyrrole-3-carboxamide (Compound No. 1-4) 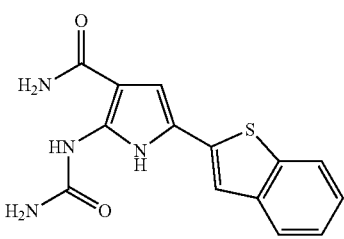 | $^1$H-NMR (400 MHz, DMSO-$d_6$) d 6.85(d, J = 2.7 Hz, 1H), 6.88 (br s, 3H), 7.25(td, J = 7.6, 1.1 Hz, 1H), 7.32(td, J = 7.6, 1.1 Hz, 1H), 7.42(br s, 1H), 7.48(s, 1H), 7.72(d, J = 7.6 Hz, 1H), 7.87(d, J = 7.6 Hz, 1H), 9.74(s, 1H), 11.30(s, 1H) |
| 2-Aminocarbonylamino-5-(benzofuran-2-yl)pyrrole-3-carboxamide (Compound No. 1-5) 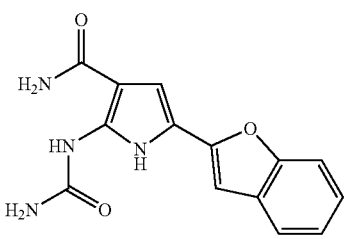 | $^1$H-NMR (400 MHz, DMSO-$d_6$) d 6.91(br s, 3H), 7.01-7.04 (m, 2H), 7.17-7.25(m, 2H), 7.46(br s, 1H), 7.49-7.59(m, 2H), 9.77(s, 1H), 11.31(s, 1H) |

| Compound | NMR |
|---|---|
| 2-Aminocarbonylamino-5-(benzothiophen-5-yl)pyrrole-3-carboxamide (Compound No. 1-6) 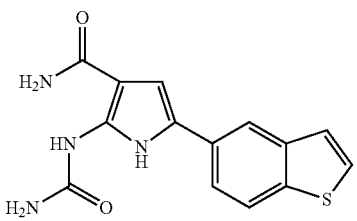 | $^1$H-NMR (500 MHz, DMSO-$d_6$) d 6.84(br s, 3H), 6.91(d, J = 3.1 Hz, 1H), 7.31(br s, 1H), 7.45-7.49(m, 2H), 7.76(d, J = 5.2 Hz, 1H), 7.92(d, J = 1.5 Hz, 1H), 7.97(d, J = 8.6 Hz, 1H), 9.66(s, 1H), 11.21(s, 1H) |
| 2-Aminocarbonylamino-5-(5-bromo-2,3-dihydrobenzofuran-7-yl)pyrrole-3-carboxamide (Compound No. 1-7) 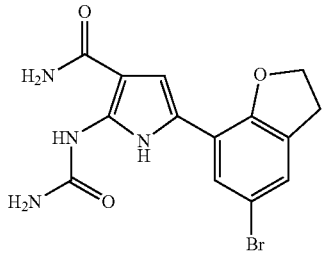 | $^1$H-NMR (400 MHz, DMSO-$d_6$) d 3.22(t, J = 8.8 Hz, 2H), 4.68 (t, J = 8.8 Hz, 2H), 6.84(br s, 3H), 6.99(d, J = 2.9 Hz, 1H), 7.18(d, J = 2.1 Hz, 1H), 7.25 (br s, 1H), 7.35(d, J = 2.1 Hz, 1H), 9.63(s, 1H), 11.55(s, 1H) |
| 2-Aminocarbonylamino-5-(benzofuran-5-yl)pyrrole-3-carboxamide (Compound No. 1-8) 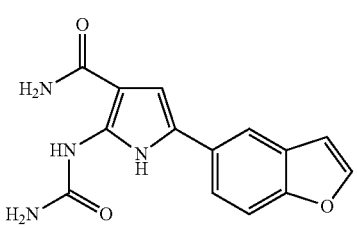 | $^1$H-NMR (400 MHz, DMSO-$d_6$) d 6.81(d, J = 3.2 Hz, 1H), 6.83 (br s, 3H), 6.97(dd, J = 2.2, 1.0 Hz, 1H), 7.29(br s, 1H), 7.40(dd, J = 8.6, 1.8 Hz, 1H), 7.59(d, J = 8.6 Hz, 1H), 7.68 (d, J = 1.8 Hz, 1H), 7.98(d, J = 2.2 Hz, 1H), 9.63(s, 1H), 11.15(s, 1H) |
| 2-Aminocarbonylamino-5-(5,5,8,8-tetramethyl-5,6,7,8-tetrahydronaphthalen-2-yl)pyrrole-3-carboxamide (Compound No. 1-9) 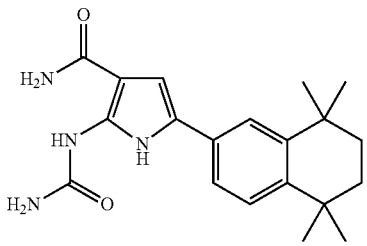 | $^1$H-NMR (400 MHz, DMSO-$d_6$) d 1.24(s, 6H), 1.28(s, 6H), 1.64(s, 4H), 6.79(br s, 3H), 6.80(d, J = 2.9 Hz, 1H), 7.02(br s, 1H), 7.16(dd, J = 8.3, 2.0 Hz, 1H), 7.30(d, J = 8.3 Hz, 1H), 7.37(d, J = 2.0 Hz, 1H), 9.59(s, 1H), 11.09 (s, 1H) |

| | |
|---|---|
| 2-Aminocarbonylamino-5-(2,3-dihydro-1,4-benzodioxin-6-yl)pyrrole-3-carboxamide (Compound No. 1-10) 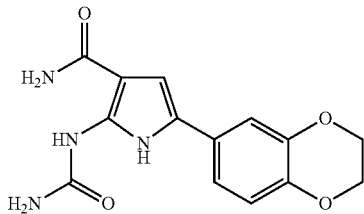 | $^1$H-NMR (400 MHz, DMSO-d$_6$) d 4.20-4.30(m, 4H), 6.69(d, J = 3.2 Hz, 1H), 6.81(br s, 3H), 6.85(d, J = 8.8 Hz, 1H), 6.87-6.90(m, 2H), 7.23(br s, 1H), 9.58(s, 1H), 11.01(s, 1H) |
| 2-Aminocarbonylamino-5-(1,3-benzodioxol-5-yl)pyrrole-3-carboxamide (Compound No. 1-11) 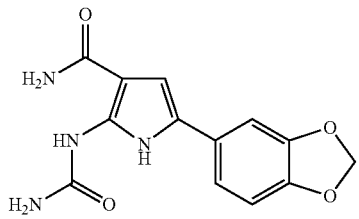 | $^1$H-NMR (400 MHz, DMSO-d$_6$) d 6.01(s, 2H), 6.70(d, J = 3.2 Hz, 1H), 6.81(br s, 3H), 6.89 (dd, J = 8.0, 1.7 Hz, 1H), 6.92 (d, J = 8.0 Hz, 1H), 6.99(d, J = 1.7 Hz, 1H), 7.21(br s, 1H), 9.58(s, 1H), 11.02(s, 1H) |
| 2-Aminocarbonylamino-5-(2,3-dihydro-1,4-benzodioxin-5-yl)pyrrole-3-carboxamide (Compound No. 1-12) 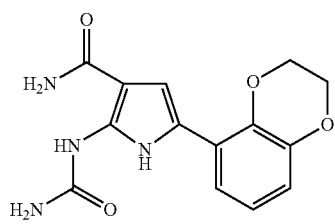 | $^1$H-NMR (400 MHz, DMSO-d$_6$) d 4.21-4.41(m, 4H), 6.65(dd, J = 7.8, 1.5 Hz, 1H), 6.77(br s, 4H), 6.82(t, J = 7.8 Hz, 1H), 6.91(d, J = 3.2 Hz, 1H), 7.02 (dd, J = 7.8, 1.5 Hz, 1H), 9.61 (s, 1H), 11.66(s, 1H) |
| 2-Aminocarbonylamino-5-(5-chloro-2,3-dimethyl-2,3-dihydrobenzofuran-7-yl)pyrrole-3-carboxamide (Compound No. 1-13) 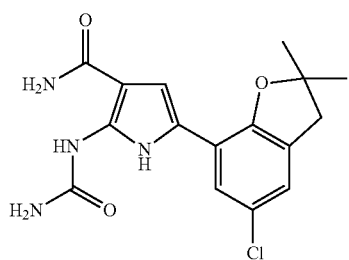 | $^1$H-NMR (400 MHz, DMSO-d$_6$) d 1.47(s, 6H), 3.04(s, 2H), 6.85(br s, 3H), 6.95(d, J = 2.9 Hz, 1H), 7.01(d, J = 2.2 Hz, 1H), 7.19(d, J = 2.2 Hz, 1H), 7.22(br s, 1H), 9.60(s, 1H), 11.79(s, 1H) |

| Compound | ¹H-NMR |
|---|---|
| 2-Aminocarbonylamino-5-(3,5-dimethylbenzothiophen-2-yl)pyrrole-3-carboxamide (Compound No. 1-14) 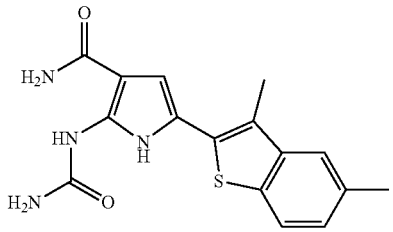 | ¹H-NMR (400 MHz, DMSO-d$_6$) d 2.44(s, 3H), 2.45(s, 3H), 6.84(d, J = 3.2 Hz, 1H), 6.88 (br s, 3H), 7.15(dd, J = 8.2, 1.1 Hz, 1H), 7.48(br s, 1H), 7.54(s, 1H), 7.76(d, J = 8.2 Hz, 1H), 9.71(s, 1H), 11.25 (s, 1H) |
| 2-Aminocarbonylamino-5-(3-methylbenzothiophen-2-yl)pyrrole-3-carboxamide (Compound No. 1-15) 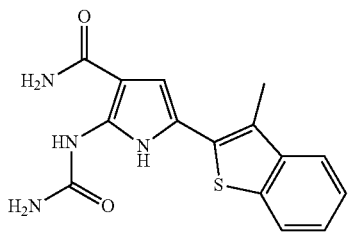 | ¹H-NMR (400 MHz, DMSO-d$_6$) d 2.48(s, 3H), 6.86(d, J = 2.9 Hz, 1H), 6.94(br s, 3H), 7.32 (m, 1H), 7.40(m, 1H), 7.48(br s, 1H), 7.74(d, J = 7.7 Hz, 1H), 7.89(d, J = 7.7 Hz, 1H), 9.72 (s, 1H), 11.28(s, 1H) |
| 2-Aminocarbonylamino-5-(5-chloro-2,3-dihydrobenzofuran-7-yl)pyrrole-3-carboxamide (Compound No. 1-16) 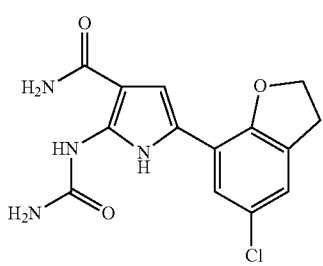 | ¹H-NMR (400 MHz, DMSO-d$_6$) d 3.21(t, J = 8.8 Hz, 2H), 4.68 (t, J = 8.8 Hz, 2H), 6.84(br s, 3H), 6.99(d, J = 2.9 Hz, 1H), 7.06(d, J = 2.2 Hz, 1H), 7.21 (d, J = 2.2 Hz, 1H), 7.24(br s, 1H), 9.64(s, 1H), 11.55(s, 1H) |
| 2-Aminocarbonylamino-5-(1,3-benzothiazol-2-yl)pyrrole-3-carboxamide (Compound No. 1-17) 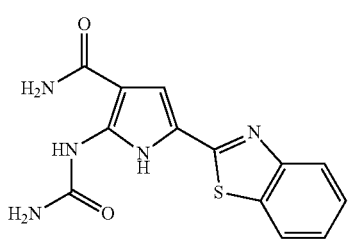 | ¹H-NMR (400 MHz, DMSO-d$_6$) d 7.03(br s, 3H), 7.28-7.40 (m, 2H), 7.46(t, J = 7.6 Hz, 1H), 7.57(br s, 1H), 7.91(s, J = 7.6 Hz, 1H), 8.02(d, J = 7.6 Hz, 1H), 9.86(s, 1H), 11.49(s, 1H) |

| Compound | NMR |
|---|---|
| 2-Aminocarbonylamino-5-(3-oxo-3,4-dihydro-2H-1,4-benzoxazin-6-yl)pyrrole-3-carboxamide (Compound No. 1-18) 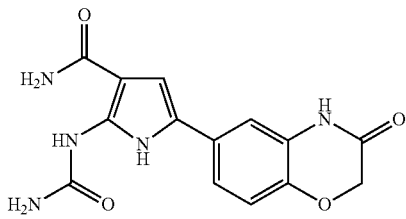 | $^1$H-NMR (400 MHz, DMSO-$d_6$) d 4.56(s, 2H), 6.70(d, J = 2.9 Hz, 1H), 6.86(br s, 3H), 6.90-7.03(m, 3H), 7.35(br s, 1H), 9.65(s, 1H), 10.75(s, 1H), 11.07(s, 1H) |
| 2-Aminocarbonylamino-5-(3-oxo-3,4-dihydro-2H-1,4-benzothiazin-6-yl)pyrrole-3-carboxamide (Compound No. 1-19) 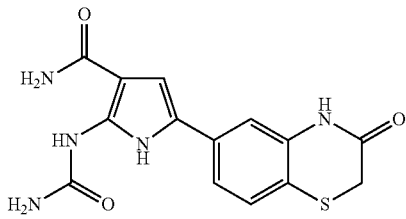 | $^1$H-NMR (400 MHz, DMSO-$d_6$) d 3.47(s, 2H), 6.81(d, J = 3.2 Hz, 1H), 6.87(br s, 3H), 7.00-7.08(m, 2H), 7.30(d, J = 8.8 Hz, 1H), 7.38(br s, 1H), 9.68(s, 1H), 10.58(s, 1H), 11.14(s, 1H) |
| 2-Aminocarbonylamino-5-(indol-6-yl)pyrrole-3-carboxamide (Compound No. 1-20) 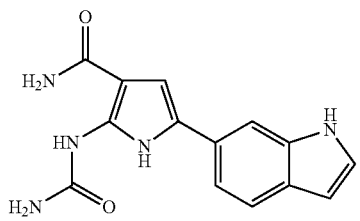 | $^1$H-NMR (400 MHz, DMSO-$d_6$) d 6.39(m, 1H), 6.77(d, J = 3.2 Hz, 1H), 6.84(br s, 3H), 7.11 (dd, J = 8.3, 1.5 Hz, 1H), 7.29 (br s, 1H), 7.31(t, J = 2.7 Hz, 1H), 7.39(s, 1H), 7.52(d, J = 8.3 Hz, 1H), 9.63(s, 1H), 11.05(s, 1H), 11.11(s, 1H) |

Example 2

2-Aminocarbonylamino-4-chloro-5-(2-naphthyl)pyrrole-3-carboxamide (Compound No. 2-1)

A solution of 2-aminocarbonylamino-5-(2-naphthyl)pyrrole-3-carboxamide (Compound No. 1-1, 92 mg, 0.31 mmol) and N-chlorosuccinimide (46 mg, 0.34 mmol) in anhydrous N,N-dimethylformamide (2 mL) was stirred at 60° C. for 2 hours. After cooling, water (10 mL) was added thereto, the precipitated solid was filtered off, and washed with water (10 mL) and acetone (10 mL). The obtained solid was dried at 50° C. under reduced pressure to give the target compound (46 mg) as a pale brown solid (Yield 45%).

| Compound | NMR |
|---|---|
| 2-Aminocarbonylamino-4-chloro-5-(2-naphthyl)pyrrole-3-carboxamide (Compound No. 2-1) 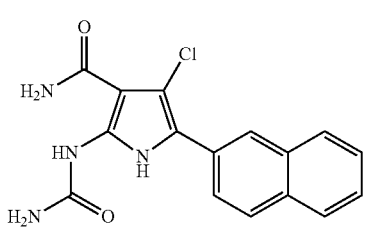 | $^1$H-NMR (400 MHz, DMSO-$d_6$) d 6.95(br s, 3H), 7.37(br s, 1H), 7.47-7.58(m, 2H), 7.78 (dd, J = 8.5, 2.0 Hz, 1H), 7.91(d, J = 7.1 Hz, 1H), 7.94-8.02(m, 2H), 8.11(d, J = 1.5 Hz, 1H), 9.85(s, 1H), 11.52(s, 1H) |

Example 3

2-Aminocarbonylamino-5-(2,3-dihydrobenzofuran-7)pyrrole-3-carboxamide (Compound No. 3-1)

10% Palladium on activated carbon (0.01 g) was added to a suspension of 2-aminocarbonylamino-5-(5-bromo-2,3-dihydrobenzofuran-7-yl) pyrrole-3-carboxamide (Compound No. 1-7, 45 mg, 0.12 mmol) in methanol-anhydrous N,N-dimethylformamide (2:1) (1.5 mL) and the mixture was stirred at room temperature overnight under hydrogen gas atmosphere. After the insoluble solid was filtered out, the filtrate was concentrated in vacuo, and water (5 mL) was added to the residue. The precipitated solid was filtered off and washed with water (5 mL). The solid was dried at 40° C. under reduced pressure to give the target compound (21 mg) as a pink solid (Yield 60%).

| 2-Aminocarbonylamino-5-(2,3-dihydrobenzofuran-7-yl)pyrrole-3-carboxamide (Compound No. 3-1) | $^1$H-NMR (400 MHz, DMSO-$d_6$) d 3.20(t, J = 8.8 Hz, 2H), 4.64 (t, J = 8.8 Hz, 2H), 6.78(br s, 3H), 6.82-6.91(m, 2H), 7.03 (dd, J = 7.1, 1.2 Hz, 1H), 7.22 (d, J = 7.8 Hz, 1H), 7.30(br s, 1H), 9.64(s, 1H), 11.54(s, 1H) |
|---|---|

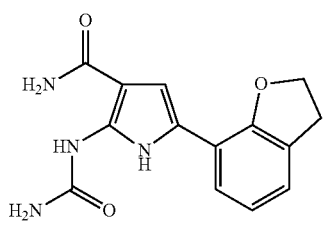

Further, commercially available compounds are compounds which is listed on product catalogs published by Sigma-Ardrich, Wako Pure Chemical Industries Ltd., Kanto Chemical Co., Inc., Tokyo Chemical Industry Co., Ltd., Nacalai Tesque Inc., and so on from 2006 to 2008.

Preparation Examples

Hereinafter, typical preparation examples of the present compound will be shown.

1) Tablet (in 150 mg)

| | |
|---|---|
| The present compound | 1 mg |
| Lactose | 100 mg |
| Cornstarch | 40 mg |
| Calcium carboxymethyl cellulose | 4.5 mg |
| Hydroxypropyl cellulose | 4 mg |
| Magnesium stearate | 0.5 mg |

A tablet of the above-mentioned formulation is coated using 3 mg of a coating agent (for example, a conventional coating agent such as hydroxypropylmethyl cellulose, macrogol or a silicone resin), whereby a desired tablet can be obtained. In addition, a desired tablet can be obtained by appropriately changing the kinds and/or amounts of the present compound and additives.

2) Capsule (in 150 mg)

| | |
|---|---|
| The present compound | 5 mg |
| Lactose | 135 mg |
| Calcium carboxymethyl cellulose | 4.5 mg |
| Hydroxypropyl cellulose | 4 mg |
| Magnesium stearate | 1.5 mg |

A desired capsule can be obtained by appropriately changing the kinds and/or amounts of the present compound and additives.

3) Eye drop (in 100 mL)

| | |
|---|---|
| The present compound | 100 mg |
| Sodium chloride | 900 mg |
| Polysorbate 80 | 500 mg |
| Sodium hydroxide | q.s. |
| Hydrochloric acid | q.s. |
| Sterile purified water | q.s. |

A desired eye drop can be obtained by appropriately changing the kinds and/or the amounts of the present compound and additives.

[Pharmacological Tests]

1. Test for Measurement of Inhibitory Activity Against IL-6 Production

An inhibitory effect on TNF-α-induced IL-6 production in normal human skin fibroblast-derived CCD-1059Sk cells (ATCC No. CRL-2072) was evaluated. The amount of IL-6 was determined by the homogeneous time-resolved fluorescence method using HTRF™ Human IL-6 kit (Cat. No. 62IL6PEB, manufactured by CIS-Bio international, Inc.). Specific test methods will be described below.

(Preparation of Test Compound Solution)

After a test compound was dissolved in dimethyl sulfoxide, the resulting solution was diluted with D-MEM medium containing 0.1% heat-inactivated fetal bovine serum, 0.1 mM MEM non-essential amino acid solution, 100 U/mL penicillin and 100 μg/mL streptomycin (hereinafter referred to as "medium"), whereby a 40 μM test compound solution was prepared.

(Test Method and Measurement Method)

1) CCD-1059Sk cells prepared at a density of $3 \times 10^5$ cells/mL were inoculated in a 384-well plate in an amount of 10 μL per well such that the cell density was $3 \times 10^3$ cells/well.

2) After the plate was incubated at 37° C. for several hours in a $CO_2$ incubator, 5 μL of the test compound solution was added to each well.

3) After the plate was incubated at 37° C. for 1 hour in a $CO_2$ incubator, 5 μL of a 40 ng/mL TNF-α solution was added to each well.

4) After the plate was incubated at 37° C. for 16 hours in a $CO_2$ incubator, 10 μL of a cryptate-labeled anti-IL-6 antibody and an XL665-labeled anti-IL-6 antibody containing potassium fluoride were added to each well.

5) After the plate was incubated at room temperature for several hours, a fluorescence intensity ratio (665 nm/620 nm) was determined for each well using a multimode plate reader Analyst™ HT (manufactured by Molecular Device Corporation) and Criterion Host software version 2.00 (manufactured by Molecular Device Corporation), and then, the amount of IL-6 was calculated.

6) The same procedures as in the above 1) to 5) were performed except that 0.4% dimethyl sulfoxide was added in place of the test compound, and the obtained result was designated as the control.

7) The same procedures as in the above 1) to 5) were performed except that 0.4% dimethyl sulfoxide and the medium were added in place of the test compound and the TNF-α solution, respectively, and the obtained result was designated as the background.
(Calculation Formula of IL-6 Production Inhibition Ratio)
An IL-6 production inhibition ratio (%) was calculated from the following equation.

IL-6 Production Inhibition Ratio(%)=100×{1−
[(Amount of IL-6 for Test Compound)−(Amount
of IL-6 for Background)]/[(Amount of IL-6 for
Control)−(Amount of IL-6 for Background)]}

(Evaluation Results)
As an example of the evaluation results, the IL-6 production inhibition ratios (%) for the test compounds (Compound No. 1-1, 1-5, 1-6, 1-8, 1-12, 1-15 and 3-1) at 10 μM are shown in Table I.

TABLE I

|  | Inhibition ratio (%) |
| --- | --- |
| Compound No. 1-1 | 90 |
| Compound No. 1-5 | 98 |
| Compound No. 1-6 | 95 |
| Compound No. 1-8 | 86 |
| Compound No. 1-12 | 97 |
| Compound No. 1-15 | 98 |
| Compound No. 3-1 | 100 |

The inhibition ratio which is 100% or more is indicated to be 100%.

As shown in Table I, the present compounds exhibited an excellent inhibitory activity against IL-6 production. Accordingly, the present compounds can be used as an inhibitor of IL-6 production and are useful as a preventive and/or therapeutic agent for the diseases considered to be associated with IL-6, ocular inflammatory diseases or the like.

Industrial Applicability

The present invention provides a novel pyrrole derivative having, as substituents, a ureido group, an aminocarbonyl group, and a bicyclic group which may have a substituent or a salt thereof. The present compound has an excellent inhibitory activity against IL-6 production and is therefore useful as an inhibitor of IL-6 production, a preventive and/or therapeutic agent for a disease considered to be associated with IL-6, a preventive and/or therapeutic agent for an ocular inflammatory disease.

The invention claimed is:

1. A compound represented by the following formula (1) or a salt thereof:

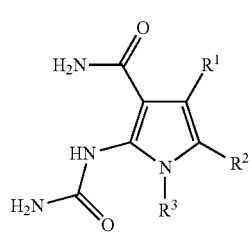

wherein $R^1$ represents a halogen atom, a hydrogen atom, a lower alkyl group which may have a substituent, a formyl group, or a lower alkylcarbonyl group which may have a substituent;

$R^2$ represents a bicyclic hydrocarbon group which may have a substituent or a bicyclic heterocyclic group which may have a substituent;
$R^3$ represents a hydrogen atom, a lower alkyl group which may have a substituent, an aryl group which may have a substituent, or an acyl group.

2. The compound or a salt thereof according to claim 1, wherein, in the formula (1),
$R^1$ represents a halogen atom or a hydrogen atom;
$R^2$ represents a bicyclic hydrocarbon group which may have a substituent or a bicyclic heterocyclic group which may have a substituent;
$R^3$ represents a hydrogen atom.

3. The compound or a salt thereof according to claim 2, wherein, in the formula (1),
in the case where $R^2$ represents a bicyclic hydrocarbon group which may have a substituent, the bicyclic hydrocarbon group is naphthalene or tetrahydronaphthalene ring.

4. The compound or a salt thereof according to claim 2, wherein, in the formula (1),
in the case where $R^2$ represents a bicyclic heterocyclic ring which may have a substituent, the bicyclic heterocyclic group is indole, benzofuran, dihydrobenzofuran, benzodioxole, dihydrobenzodioxine, benzothiophene, benzoxazine, benzothiazole or benzothiazine ring.

5. A compound or a salt thereof selected from the group consisting of
2-Aminocarbonylamino-5-(2-naphthyl)pyrrole-3-carboxamide,
2-Aminocarbonylamino-5-(benzofuran-2-yl)pyrrole-3-carboxamide,
2-Aminocarbonylamino-5-(benzothiophen-5-yl)pyrrole-3-carboxamide,
2-Aminoacarbonylamino-5-(benzofuran-5-yl)pyrrole-3-carboxamide,
2-Aminocarbonylamino-5-(2,3-dihydro-1,4-benzodioxin-5-yl)pyrrole-3-carboxamide,
2-Aminocarbonylamino-5- (3-methylbenzothiophen-2-yl) pyrrole-3-carboxamide, and
2-Aminocarbonylamino-5-(2,3-dihydrobenzofuran-7-yl) pyrrole-3-carboxamide.

6. A pharmaceutical composition comprising at least one compound or a salt thereof according to any one of claims 1 to 4 and a pharmaceutically acceptable salt thereof.

7. The pharmaceutical composition according to claim 6, which is a therapeutic agent for a disease considered to be associated with IL-6.

8. The pharmaceutical composition according to claim 6, which is a therapeutic agent for an ocular inflammatory disease.

9. The pharmaceutical composition according to claim 8, wherein the ocular inflammatory disease is age-related macular degeneration, diabetic retinopathy, diabetic macular edema, keratitis, conjunctivitis or uveitis.

10. A method for treating an ocular inflammatory disease, which comprises administering to a patient a pharmaceutically effective amount of the compound or a salt thereof according to any one of claims 1 to 4.

11. The method for treating an ocular inflammatory disease according to claim 10, wherein the ocular inflammatory disease is age-related macular degeneration, diabetic retinopathy, diabetic macular edema, keratitis, conjunctivitis or uveitis.

* * * * *